US005861147A

United States Patent [19]
Dodd et al.

[11] Patent Number: 5,861,147
[45] Date of Patent: Jan. 19, 1999

[54] METHODS FOR CONTROLLING ENVIRONMENTAL ODORS ON THE BODY USING COMPOSITIONS COMPRISING UNCOMPLEXED CYCLODEXTRINS AND PERFUME

[75] Inventors: Michael Thomas Dodd, Edgewood, Ky.; Toan Trinh, Maineville, Ohio; Robert Gregory Bartolo; Juliet Marie Lucas, both of Cincinnati, Ohio

[73] Assignee: The Procter & Gamble Company, Cincinnati, Ohio

[21] Appl. No.: 871,791

[22] Filed: Jun. 9, 1997

[51] Int. Cl.[6] .......................... A61K 7/32; A61K 25/00; A61K 33/10; A61K 33/24
[52] U.S. Cl. .................... 424/65; 422/5; 424/67; 424/69; 424/76.1; 424/76.2; 424/76.21; 424/76.4; 424/76.8; 424/78.03; 424/405; 424/642; 424/715; 424/717
[58] Field of Search ...................... 424/65, 67, 69, 424/76.1, 76.2, 76.21, 76.4, 76.8, 78.03, 405, 642, 715, 717; 422/5

[56] References Cited

U.S. PATENT DOCUMENTS

| | | | |
|---|---|---|---|
| 2,544,093 | 3/1951 | Kilgore | 252/1 |
| 3,074,891 | 1/1963 | Kulka | 252/305 |
| 4,278,658 | 7/1981 | Hooper et al. | 424/65 |
| 4,382,079 | 5/1983 | Marschner | 424/65 |
| 4,822,602 | 4/1989 | Sabatelli | 424/65 |
| 4,904,524 | 2/1990 | Yoh | 428/311.3 |
| 5,429,628 | 7/1995 | Trinh et al. | 604/359 |
| 5,486,355 | 1/1996 | Berschied, Jr. | 424/65 |
| 5,512,199 | 4/1996 | Khan et al. | 252/106 |
| 5,514,367 | 5/1996 | Lentini et al. | 424/59 |
| 5,518,727 | 5/1996 | Lajoie et al. | 424/400 |
| 5,540,853 | 7/1996 | Trinh et al. | 510/101 |
| 5,552,378 | 9/1996 | Trinh et al. | 512/3 |
| 5,578,563 | 11/1996 | Trinh et al. | 510/513 |
| 5,580,851 | 12/1996 | Trinh et al. | 512/4 |
| 5,593,670 | 1/1997 | Trinh et al. | 424/76.1 |
| 5,635,165 | 6/1997 | Panitch | 424/65 |
| 8,289,732 | 8/1994 | Trinh et al. . | |
| 8,289,733 | 8/1994 | Trinh et al. . | |
| 8,289,734 | 8/1994 | Cappel et al. . | |
| 8,289,735 | 8/1994 | Cappel et al. . | |
| 8,289,969 | 8/1994 | Pilosof et al. . | |
| 8,736,093 | 10/1996 | Trinh et al. . | |
| 8,736,469 | 10/1996 | Trinh et al. . | |
| 8,736,470 | 10/1996 | Lucas et al. . | |
| 8,736,471 | 10/1996 | Lucas et al. . | |
| 8,736,838 | 10/1996 | Peterson et al. . | |
| 8,738,964 | 10/1996 | Dodd et al. . | |
| 8,739,091 | 10/1996 | Peterson et al. . | |
| 8,871,042 | 6/1997 | Woo et al. . | |
| 8,871,092 | 6/1997 | Peterson et al. . | |
| 8,871,119 | 6/1997 | Woo et al. . | |
| 8,871,166 | 6/1997 | Lucas et al. . | |
| 8,871,576 | 6/1997 | Woo et al. . | |
| 8,871,577 | 6/1997 | Lucas et al. . | |
| 8,871,790 | 6/1997 | Peterson et al. . | |
| 8,871,853 | 6/1997 | Lucas et al. . | |
| 8,871,854 | 6/1997 | Lucas et al. . | |
| 8,871,855 | 6/1997 | Trinh et al. . | |
| 8,871,856 | 6/1997 | Peterson et al. . | |
| 8,871,857 | 6/1997 | Lucas et al. . | |
| 8,871,858 | 6/1997 | Lucas et al. . | |
| 8,871,860 | 6/1997 | Lucas et al. . | |
| 8,871,861 | 6/1997 | Peterson et al. . | |
| 8,889,607 | 7/1997 | Trinh et al. . | |

FOREIGN PATENT DOCUMENTS

| | | |
|---|---|---|
| 0 613 675 A1 | 9/1994 | European Pat. Off. . |
| 2201880 | 5/1974 | France . |
| 208482 B | 8/1992 | Hungary . |
| 53-41440 | 4/1978 | Japan . |
| 58-124452 | 7/1983 | Japan . |
| 61-128973 | 6/1986 | Japan . |
| 63-164953 | 7/1988 | Japan . |
| 3-170415 | 7/1991 | Japan . |
| 3-284616 | 12/1991 | Japan . |
| 5-269185 | 10/1993 | Japan . |
| 2731520 | 1/1979 | United Kingdom . |
| WO 95/17175 | 6/1995 | WIPO . |
| WO 96/04940 | 2/1996 | WIPO . |

OTHER PUBLICATIONS

Hashimoto, H., "Studies on the Industrial Production and Application of Cyclodextrins", Starch Science, vol. 36, No. 1 (1989), pp. 35–42.

H. Matsuda, et al., "Application of 2–Hydroxypropyl–β–Cyclodextrin to Perfumes and Cosmetics", The 7th International Cyclodextrins Symposium, Tokyo, Japan, Apr. 25–28, 1994, pp. 516–519.

Hashimoto, H., "Application of Cyclodextrins to Foods, Toiletries and Other Products in Japan", Ensuiko Sugar Refining Co., Ltd., pp. 13–46.

T. Loftsson, et al. "Interactions Between Preservatives and 2–Hydroxypropyl–β–Cyclodextrin", Drug Development and Industrial Pharmacy, 18(13), 1992, pp. 1477–1484.

*Primary Examiner*—Shelley A. Dodson
*Attorney, Agent, or Firm*—Kirsten K. Stone; Mary Catherine Hentz; Douglas C. Mohl

[57] ABSTRACT

The present invention encompasses methods of controlling environmental malodors on skin comprising the application to the skin of a composition comprising from about 0.1% to about 5%, by weight of the composition, of solubilized, water-soluble, uncomplexed cyclodextrin; from about 0.004% to about 2%, by weight of the composition, of a hydrophilic, volatile perfume composition comprising at least about 50% by weight of one or more hydrophilic, volatile perfume ingredients wherein each ingredient has a boiling point of about 260° or lower, and a ClogP of less than about 3.5, and an aqueous carrier. The compositions can be applied directly as a spray, poured from a bottle and applied by hand, or applied via a wipe.

17 Claims, No Drawings

METHODS FOR CONTROLLING ENVIRONMENTAL ODORS ON THE BODY USING COMPOSITIONS COMPRISING UNCOMPLEXED CYCLODEXTRINS AND PERFUME

BACKGROUND OF THE INVENTION

Daily contact with substances which leave unpleasant and/or lingering odors on an individual's body and hair is almost unavoidable. Foods such as fish, onions, garlic or other spices, cooking odors, smoke, tobacco, and gasoline are just a few of the common environmental sources of malodors in daily life.

Numerous attempts have been made to conceal unpleasant odors through the use of deodorizing compositions. These compositions typically rely on the presence of heavy fragrances or perfumes to mask odors. However, perfumes and fragrances alone are often inadequate at fully concealing malodors, and some may be irritating to the user.

Zeolites such as those marketed under the trade name Abscents® by the Union Carbide Corporation and UOP are known odor absorbers. However these commonly known solid odor absorbers, in addition to known activated charcoal odor absorbers, lose functionality when wet. Therefore, when wetted by body fluids or when carried in an aqueous solution, these odor absorbers are not preferred as they lose their desired odor absorbent characteristics. Furthermore, zeolites can cause a "harsh" feel if too much is deposited onto the skin. The white zeolite powder and the black activated charcoal can also be rather visible and unsightly when applied to body surfaces such as skin.

U.S. Pat. No. 5,534,165, to Pilosof et al., issued Jul. 9, 1996, describes aqueous, odor absorbing compositions for controlling odors on fabrics, particularly clothes. Such compositions, however, are not for use directly on the human skin.

Thus, there remains a need for improved methods for controlling environmental odors which are safe and effective for use on the entire body. Furthermore, it is desirable that a perfume is fleeting such that it indicates freshness, but is not long lasting on the user's skin. More particularly, there is a need for convenient methods of absorbing a broad spectrum of odors that are not fully suppressed by the aforementioned means.

It has been discovered that methods for such enhanced malodor control can be safely provided to the entire body by application of a mixture which is left on the skin and which incorporates odor absorbing, uncomplexed cyclodextrins and a hydrophilic, volatile perfume composition into an aqueous solution. Such methods provide a leave on mixture with optimal malodor absorbing characteristics. Moreover, it has been discovered that the aforementioned benefits may be delivered in an aqueous solution which also optionally delivers skin aid benefits to the user such as protection and/or moisturization.

These and other objects of the present invention will become readily apparent from the detailed description which follows. All percentages, ratios, and parts herein, in the Specification, Examples, and Claims are by weight unless otherwise stated. The term "g", as used herein, means gram. The term "ml", as used herein, means milliliter. The term "wt", as used herein, means weight.

SUMMARY OF THE INVENTION

The present invention encompass methods of controlling environmental malodors on skin comprising the application to the skin of a composition comprising from about 0.1% to about 5%, by weight of the composition, of solubilized, water-soluble, uncomplexed cyclodextrin; from about 0.004% to about 2%, by weight of the composition, of a hydrophilic, volatile perfume composition comprising at least about 50% by weight of one or more hydrophilic, volatile perfume ingredients wherein each ingredient has a boiling point of about 260° or lower, and a ClogP of less than about 3.5; and an aqueous carrier.

DETAILED DESCRIPTION OF THE INVENTION

The present methods comprise the application of a malodor-absorbing composition comprising solubilized, water-soluble, uncomplexed cyclodextrins and a hydrophilic, volatile perfume composition. The compositions can be applied directly as a spray, poured from a bottle and applied by hand, or applied via a pre-formed wipe which is wet with the composition when it is applied to skin. The present invention also relates to an article of manufacture comprising the environmental odor-absorbing composition incorporated into a flexible dispensing means.

The term "environmental malodors", as used herein means any odor which may be on a human or mammal which is not the result of body odor and/or body fluids. Such odors include but are not limited to odors from foods such as fish, garlic, onions, peppers and spices; cooking; smoke; tobacco; gasoline; and the like.

The term "body fluids", as used herein, includes eccrine sweat, apocrine sweat, sebum, build up of sensible moisture from transepidermal water loss, vaginal discharge, urine, and mixtures thereof. The term "body odor" as used herein means odors which are generated as a result of the natural functioning of a human or mammalian body. Such odors include, but are not limited to odors produced by microorganisms of the human or mammalian skin (i.e. bacterial decomposition of skin secretions), urine, or vaginal discharge, and mixtures thereof. The term "entire body" means the entire external surface of human or mammalian skin. The term "skin" means human or mammalian skin. The term "controlling" environmental malodors, as used herein, means absorbing, reducing or eliminating environmental malodors as determined by the human sense of smell.

A detailed description of essential and optional components of the present invention is given below.

METHOD OF USE

The present invention encompasses a method of controlling environmental malodors comprising the application of a composition comprising solubilized, water-soluble, uncomplexed cyclodextrin; a perfume composition; and an aqueous carrier. The compositions can also comprise one or more of the following optional components: a linear dimethicone having a nominal viscosity of 350 centistokes or less; low molecular weight polyols; water-soluble antimicrobial preservatives; zinc salts; water-soluble polymers; soluble carbonate and/or bicarbonate salts; chelating agents; zeolites; activated carbon; and mixtures thereof.

An "effective amount" of the compositions of the present invention, as used herein, means an amount sufficient to absorb environmental malodors to the point that it is less noticeable by the human sense of smell. While the determination of an effective amount used and the number of uses per day can be ultimately left to the discretion of the user, typically an effective amount will be from about 3.0 grams to about 0.5 grams of environmental odor-absorbing composition per use, applied from about 1 to about 15 times per day, for as many days as desired by the user.

The compositions of the present invention are topically applied directly to the skin or hair. The compositions can be delivered by placing the composition into a dispensing means and applying an effective amount via spraying or rubbing the composition onto the desired skin surface; typically the hands. Preferably the dispensing means is a wipe or, when the composition does not comprise dimethicone, a spray dispenser. Distribution of the composition of the present invention can also be achieved by using a preformed applicator such as a roller, pad, sponge, tissue, cotton ball, hand, etc.

Alternatively, when the composition does not include dimethicone, the user may combine the composition of the present invention with a wipe substance of his or her own choosing. To do this, the user simply chooses a wipe substance such as a commercial paper towel, tissue, sponge, cotton, pad, washcloth, or the like; and pours, from a bottle or other suitable container, a solution of the composition of the present invention over the chosen wipe substance and applies the composition to the desired area of the body. In this manner, the user may use as much or as little of the composition of the present invention as he/she desires, depending upon their intended use and degree of odor control necessary.

CYCLODEXTRIN

As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof.

The term "uncomplexed cyclodextrin" as used herein means that the cavities within the cyclodextrin in the solution of the present invention should remain essentially unfilled while in solution, in order to allow the cyclodextrin to absorb various odor molecules when the solution is applied to a surface. The term "water-soluble, uncomplexed cyclodextrin" as used herein means uncomplexed cyclodextrin having a minimum solubility limit of 1% (1 gram in 100 grams of water).

Non-derivatised beta-cyclodextrin can be present at a level up to its solubility limit of about 1.85% at room temperature. When beta-cyclodextrin is applied to a wipe substrate, levels higher than its solubility limit can be used.

Preferred, the cyclodextrins used in the present invention are highly water-soluble such as, alpha-cyclodextrin and/or derivatives thereof, gamma-cyclodextrin and/or it derivatives thereof, derivatised beta-cyclodextrins, and/or mixtures thereof. The derivatives of cyclodextrin consist mainly of molecules wherein some of the OH groups are converted to OR groups. Highly water-soluble cyclodextrins are those having water solubility of at least about 10 g in 100 ml of water at room temperature, preferably at least about 20 g in 100 ml of water, more preferably at least about 25 g in 100 ml of water at room temperature. The preferred highly water-soluble cyclodextrins are hydroxy propyl beta-cyclodextrin and methylated beta-cyclodextrin.

It is also preferable to use a mixture of cyclodextrins. Such mixtures absorb body odors more broadly by complexing with a wider range of odoriferous molecules having a wider range of molecular sizes. Preferred mixtures are mixtures of beta-cyclodextrin and/or its derivatives with alpha-cyclodextrin and/or its derivatives, and mixtures thereof. The levels of cyclodextrin are from about 0.1% to about 5%, preferably from about 0.2% to about 4%, more preferably from about 0.3% to about 3%, most preferably from about 0.4% to about 2%, by weight of the composition.

Concentrated compositions can also be used. When a concentrated product is used, i.e., when the level of cyclodextrin used is from about 3% to about 10%, it is preferable to dilute the composition before applying to the skin in order to avoid tacky skin feel and/or an undesirable amount of residue. Preferably the cyclodextrin is diluted with about 50% to about 2000%, more preferably with about 60% to about 1000%, most preferably with about 75% to about 500%, by weight of the composition of water.

The complexation between cyclodextrin and odorous molecules occurs rapidly in the presence of water when the solubilized cyclodextrins are first applied to the skin. Additionally, cyclodextrins which dry on the skin surfaces will once again achieve enhanced absorption capabilities when rewetted with fluids. This is convenient for the user because the cyclodextrins, while on dry skin, will not readily fill their cavities with other odors which would otherwise render them less efficient. More particularly, upon solubilization of the cyclodextrins by the body fluids or other fluids, the isolated cavities again become available to form inclusion complexes with the environmental odor molecules on the body. Thus, ultimately, the availability of solubilized uncomplexed cyclodextrin is essential for an effective and efficient odor control performance. A more complete description of the cyclodextrins and cyclodextrin derivatives useful in the present invention can be found in U.S. Pat. No. 5,534,165, Pilosof et al., issued Jul. 9, 1996, which is incorporated herein by reference in its entirety.

PERFUME COMPOSITION

The present invention contains a hydrophilic, volatile perfume composition comprising perfume ingredients. The hydrophilic perfume composition is volatile and fleeting such that the perfume is effusive and noticeable when the product is first used, but its odor impact is substantially diminished when the treated surface, e.g., skin, is dry. Preferred are perfume ingredients which are both hydrophilic and volatile.

The perfume composition is one which is safe for use on skin. The phrase "safe for use on skin", as used herein, means that the composition provides the desired benefit without undue side effects.

A volatile and hydrophilic perfume ingredient is characterized by its boiling point ("B.P.") and its octanol/water partition coefficient ("P"). The boiling points of many perfume ingredients are given in, e.g., "Perfume and Flavor Chemicals (Aroma Chemicals)," Steffen Arctander, published by the author, 1969, incorporated herein by reference. The octanol/water partition coefficient of a perfume ingredient is the ratio between its equilibrium concentrations in octanol and in water. Since the partition coefficients of the preferred perfume ingredients have high values, they are more conveniently given in the form of their logarithm to the base 10, logp. LogP values which are calculated are referred to as "ClogP". "ClogP" values are readily calculated from a program called "CLOGP" which is available from Daylight Chemical Information Systems, Inc., Irvine Calif. Octanol/water partition coefficients are described in detail in U.S. Pat. No. 5,578,563, to Trinh, issued Nov. 26, 1996, incorporated herein by reference in its entirety. The preferred perfume ingredients have a B.P., determined at the normal, standard pressure of about 760 mm Hg, of about 260° C. or lower, preferably less than about 250° C., and a ClogP or an experimental logP, of less than about 3.5, and preferably of less than about 3.0.

Non-limiting examples of preferred hydrophilic, volatile perfume ingredients are allyl caproate, amyl acetate, amyl propionate, anisic aldehyde, anisole, benzaldehyde, benzyl acetate, benzyl acetone, benzyl alcohol, benzyl formate, benzyl isovalerate, benzyl propionate, beta gamma hexenol, camphor gum, laevo-carveol, d-carvone, laevo-carvone, cinnamyl formate, cis-jasmone, cis-3-hexenyl acetate, cuminic alcohol, cuminic aldehyde, Cyclal C, dimethyl benzyl carbinol, dimethyl benzyl carbinyl acetate, ethyl acetate, ethyl acetoacetate, ethyl amyl ketone, ethyl benzoate, ethyl butyrate, ethyl hexyl ketone, ethyl phenyl acetate, eucalyptol, fenchyl alcohol, flor acetate (tricyclo decenyl acetate), frutene (tricyclo decenyl propionate), geraniol, hexenol, hexenyl acetate, hexyl acetate, hexyl formate, hydratropic alcohol, hydroxycitronellal, isoamyl alcohol, isomenthone, isopulegyl acetate, isoquinoline, ligustral, linalool, linalool oxide, linalyl formate, menthone, methyl acetophenone, methyl amyl ketone, methyl anthranilate, methyl benzoate, methyl benzyl acetate, methyl eugenol, methyl heptenone, methyl heptine carbonate, methyl heptyl ketone, methyl hexyl ketone, methyl phenyl carbinyl acetate, methyl salicylate, nerol, nonalactone, octalactone, octyl alcohol (octanol-2), para-cresol, para-cresyl methyl ether, para-methyl acetophenone, phenoxy ethanol, phenyl acetaldehyde, phenyl ethyl acetate, phenyl ethyl alcohol, phenyl ethyl dimethyl carbinol, prenyl acetate, propyl butyrate, pulegone, rose oxide, safrole, terpineol, viridine, and mixtures thereof.

Examples of other hydrophilic, volatile perfume ingredients useful herein are allyl heptoate, anethol, carvacrol, cinnamic alcohol, citral, citronellol, citronellyl nitrile, cyclohexyl ethyl acetate, dihydro myrcenol, ethyl methyl phenyl glycidate, eugenol, fenchyl acetate, gamma-nonalactone, geranyl acetate, geranyl formate, geranyl nitrile, hexenyl isobutyrate, indole, alpha-ionone, isobornyl acetate, isobutyl benzoate, isononyl alcohol, isomenthol, isopulegol, linalyl acetate, methyl chavicol, methyl-N-methyl anthranilate, neral, neryl acetate, nonyl aldehyde, para-isopropyl phenylacetaldehyde, para-methoxy acetophenone, phenyl hexanol, terpinyl acetate, veratrol, and mixtures thereof.

The hydrophilic, volatile perfume composition is at a level of from about 0.004% to about 2%, preferably from about 0.006% to about 1%, and more preferably from about 0.007% to about 0.2%, by weight of the environmental odor control composition. The hydrophilic, volatile perfume composition comprises at least 4 different hydrophilic, volatile perfume ingredients, preferably at least 5 different hydrophilic, volatile perfume ingredients, more preferably at least 6 different hydrophilic, volatile perfume ingredients, and even more preferably at least 7 different hydrophilic, volatile perfume ingredients.

Furthermore, the hydrophilic, volatile perfume composition contains at least about 50 wt. % of hydrophilic, volatile perfume ingredients, preferably at least about 55 wt. % of hydrophilic, volatile perfume ingredients, more preferably at least about 60 wt. % of hydrophilic, volatile perfume ingredients, and even more preferably at least about 70 wt. % of hydrophilic, volatile perfume ingredients. Most common perfume ingredients which are derived from natural sources are composed of a multitude of components. When each such material is used in the formulation of hydrophilic, volatile perfume compositions of the present invention, it is counted as one ingredient, for the purpose of defining the invention. Synthetic reproductions of such natural perfume ingredients are also often comprised of a multitude of components and are counted as one ingredient for the purpose of defining the invention.

Some of the hydrophilic, volatile perfume ingredients can optionally be replaced by hydrophilic, residual perfume ingredients. The optional hydrophilic, residual perfume ingredients have a B.P., measured at the normal, standard pressure, higher than about 260° C., and an experimental logP or ClogP of less than about 3.5. Thus, when a perfume composition is composed of some preferred hydrophilic, volatile ingredients and some hydrophilic, residual ingredients, the perfume effect is longer lasting when the product is used. Non-limiting examples of optional hydrophilic, residual perfume ingredients, useful herein are amyl benzoate, benzophenone, dihydro isojasmonate, isoeugenol, methyl cinnamate, methyl dihydrojasmonate, beta-methyl naphthyl ketone, 2-methoxy naphthalene, delta-nonalactone, vanillin, yara-yara, and mixtures thereof.

When hydrophilic, residual perfume ingredients are used in combination with the hydrophilic, volatile perfume ingredients in the perfume compositions, the weight ratio of hydrophilic, volatile perfume ingredients to hydrophilic, residual perfume ingredients is typically greater than about 1, preferably greater than about 1.3, more preferably greater than about 1.5, and even more preferably greater than about 2. In this case, the perfume compositions contain at least about 50 wt. % of the combined hydrophilic, volatile perfume ingredients and hydrophilic, residual perfume ingredients, preferably at least about 55 wt. % of the combined perfume ingredients, more preferably at least about 60 wt. % of the combined perfume ingredients, and even more preferably at least about 70 wt. % of the combined perfume ingredients.

In the perfume art, some auxiliary materials having no odor, or a low odor, are used, e.g., as solvents, diluents, extenders or fixatives. Non-limiting examples of these materials are ethyl alcohol, carbitol, dipropylene glycol, diethyl phthalate, triethyl citrate, isopropyl myristate, and benzyl benzoate. These materials may be used for solubilizing or diluting some solid or viscous perfume ingredients to improve handling and/or formulating. These materials are useful in the hydrophilic, volatile perfimie compositions, but are not counted in the calculation of the limits for the definition/formulation of the hydrophilic, volatile perfume compositions of the present invention.

Hydrophobic perfume ingredients, which should be minimized in odor controlling compositions of the present invention, are those having a ClogP. of more than about 3.5. Normally, some hydrophobic perfume ingredients can be used in small amounts, e.g., to improve product odor.

AQUEOUS CARRIER

The cyclodextrins useful in the methods of the present invention should be solubilized in and dispersed in an aqueous carrier. The dilute aqueous solution provides the maximum separation of cyclodextrin molecules on the skin and maximizes the chance that an odor molecule will interact with a cyclodextrin molecule. An aqueous carrier is also beneficial in that it provides a clean, convenient means for applying the cyclodextrin to the desired skin sites. Additionally, an aqueous carrier may impart a degree of cleaning power in and of itself via washing away skin cell debris and skin secretions which bacteria feed upon, as well as the bacteria themselves.

The term "aqueous carrier", as used herein, means water and/or any water soluble materials suitable for use as solvents. Any water may be used, such as distilled, deionized, or tap water. Water not only serves as the liquid carrier for the cyclodextrins, but it also facilitates the complexation reaction between the cyclodextrin molecules and any malodorous molecules that are on the skin site when the composition is applied.

The aqueous carrier of the present invention will typically comprise from about 80% to about 98%, and preferably from about 85% to about 95%, by weight of the composition. In compositions comprising only cyclodextrins, a perfume composition and an aqueous carrier, the aqueous carrier is present at a level of from about 95% to about 99.9%, preferably from about 96% to about 99.8%, and more preferably from about 97% to about 99.7%, by weight of the composition.

DIMETHICONE

The compositions may also comprise an effective level of dimethicone, which aids in preventing or reducing skin irritation and also may contribute other benefits such as reducing skin-to-skin friction. An "effective level" of dimethicone, as used herein, is a level which effectively provides the desired skin benefits of dimethicone. The dimethicones used in the present invention must be linear dimethicones having nominal viscosities of 350 centistokes or less. Preferred is a linear dimethicones having a nominal viscosities of about 50 to about 100 centistokes, available as Dow Corning ® 200 Fluid. Typically, the dimethicone is present at a level of from about 0.5% to about 30% preferably from about 1% to about 2%, by weight of the composition.

ANTIMICROBIAL PRESERVATIVE

The compositions may optionally but preferably contain solubilized, mild, water-soluble, antimicrobial preservatives which are effective for inhibiting and/or regulating microbial growth in the composition. Contamination of the compositions by microorganisms and subsequent microbial growth can result in unsightly or malodorous compositions. Similarly, microorganisms are typically found in cyclodextrin supplies and their growth in aqueous solutions is possible. The inclusion of the antimicrobial preservatives aids in increasing storage stability of the present invention. When included for preservative action, the water-soluble antimicrobials are present in an effective amount. The phrase "effective amount" of water-soluble antimicrobial preservative as used herein means a level sufficient to prevent spoilage, or prevent growth of microorganisms inadvertently added to the s composition, for a specific period of time. If antimicrobial action on the skin is desired, the water-soluble antimicrobials must be present at a level effective to perform the preservative action discussed above and to kill and/or prevent growth of microorganisms on the skin.

Antimicrobials useful herein include biocidal and biostatic compounds (substances that kill microorganisms and/or regulate the growth of microorganisms). Suitable water-soluble antimicrobial preservatives have a solubility of 0.3% or greater. In addition, suitable preservatives are those which can come into contact with skin without high irritation potential. Preservatives suitable for use in the present compositions are fully described in The Theory and Practice of Industrial Pharmacy, by Lachman, Lieberman, Kanig, 3rd. Edition, pages 466–467 and 520–522 (1986), and U.S. Pat. No. 5,534,165, to Pilosof et al., issued Jul. 9, 1996, both of which are incorporated herein by reference.

It is preferable to use a broad spectrum preservative such as one that is effective both on bacteria (both gram positive and gram negative) and fungi. A limited spectrum preservative such as one that is only effective on a single group of microorganisms, for example fungi, can be used in combination with a broad spectrum preservative or other limited spectrum preservatives with complimentary and/or supplementary activity. A mixture of broad spectrum preservatives can also be used.

Preferred water-soluble preservatives include the following: sodium hydroxymethylglycinate (i.e. Suttocide® A., from Sutton Labs Chatham, N.J.), cyclic organic nitrogen compounds including imidazolidinedione compounds (such as dimethyloldimethylhydantoin i.e., Glydant® Plus from Lonza, Fair Lawn, N.J.; diazolidinyl urea and imidazolidinyl urea) and polymethoxy bicyclic oxazolidine; phenyl and phenoxy compounds including benzyl alcohol, 2-phenoxyethanol and hexamidine isethionate; quaternary ammonium compounds including polyhexamethylene biguanide; low molecular weight aldehydes including formaldehyde and glutaraldehyde; halogenated compounds including chlorhexidine, chlorobutanol, and dibromopropamidine; and mixtures thereof.

Preferred levels of preservative are from about 0.0001% to about 0.6%, more preferably from about 0.0002% to about 0.55%, most preferably from about 0.0003% to about 0.5%, by weight of the composition.

pH

Aqueous compositions of the present invention should have a pH of from about 3 to about 10, preferably from about 3.5 to about 8, more preferably from about 3.5 to about 6. Some conventional buffering agents are known in the prior art which may be used to adjust the pH to the desired level if necessary. For example, combinations of salts and acids, such as the following examples: sodium lactate, sodium citrate, potassium phosphate, lactic acid, citric acid, phosphoric acid, sodium hydroxide, and hydrochloric acid are useful. Some of the effectiveness of these ingredients may be lost as they complex with the cyclodextrin, so care is taking in formulating to adjust for that. Other optional buffers appear in The Theory and Practice of Industrial Pharmacy, Lachman, Lieberman and Kanig, Third Edition, incorporated herein by reference.

OTHER COMPONENTS

The compositions may also optionally comprise low molecular weight polyols. The phrase "low molecular weight polyols", as used herein, refers to linear organic compounds with more than one alcohol functional group per molecule wherein the molecular weight is less than 95. Low molecular weight polyols with relatively high boiling points, as compared to water, such as propylene glycol and glycerol are preferred ingredients for improving Whiz environmental malodor control performance of the present compositions. Cyclodextrins prepared by processes that result in a level of such polyols are highly desirable, since they can be used without removal of the polyols.

Optimally, the low molecular weight polyols will be added at a level effective to assist in complex formation without significantly reducing available cyclodextrin capacity to absorb the malodor molecules having larger sizes. Typically, low molecular weight polyols are added to the composition of the present invention at a level of from about 0.01% to about 1%, by weight of the composition, preferably from about 0.02% to about 0.5%, more preferably from about 0.03% to about 0.3%, by weight of the composition.

The compositions may also optionally contain adjunct odor-controlling materials, such as zinc salts, water-soluble cationic polymers, water-soluble anionic polymers, water-soluble carbonate salts, water-soluble bicarbonate salts, zeolites, and activated carbon; chelating agents; colorants; and/or antiperspirants.

Optionally, but highly preferred, the present invention can include zinc salts for added odor absorption and/or antimicrobial benefit for the cyclodextrin solution. Zinc compounds have been used most often for their ability to ameliorate malodor, e.g., in mouth wash products, as disclosed in U.S. Pat. Nos. 4,325,939, issued Apr. 20, 1982 and 4,469,674, issued Sep. 4, 1983, to N. B. Shah, et al., both of which are incorporated herein by reference in their entireties. Highly-ionized and water soluble zinc salts such as zinc chloride provide the best source of zinc ions. The zinc salt, zinc phenolsulfonate, is preferred for use in the skin composition of the present invention; although others may also fall within the scope of the present invention. However, care must be taken in selecting zinc salts, as well as their levels, since some may be irritants to the skin and therefore are not preferred for use in the present invention.

These zinc salts aid in absorbing low molecular weight amine and sulfur-containing compounds. Low molecular weight amines and/or low molecular weight sulfur-containing materials such as sulfide and mercaptans; are components of many types of malodors such as food odors (garlic, onion), breath odor, urine odors, and particularly body/perspiration odor.

When zinc salts are added to the composition of the present invention they are typically present at a level of from about 0.1% to about 10%, preferably from about 0.2% to about 8%, more preferably from about 0.3% to about 5%, by weight of the composition.

Some water-soluble polymers such as water-soluble cationic polymer and water-soluble anionic polymers can be used in the composition of the present invention to provide additional odor control benefits. Water-soluble cationic polymers such as those containing amino functionalities, amido functionalities, and mixtures thereof, are useful in the present invention to control certain acid-type odors. Water-soluble anionic polymers such as polyacrylic acids and their water-soluble salts are useful in the present invention to control certain amine-type odors. Preferred polyacrylic acids and their alkali metal salts have an average molecular weight of less than about 20,000, more preferably less than 5,000. Polymers containing sulfonic acid groups, phosphoric acid groups, phosphonic acid groups, and their water-soluble salts, and mixtures thereof, and mixtures with carboxylic acid and carboxylate groups, are also suitable.

Water-soluble polymers containing both cationic and anionic functionalities are also suitable. Examples of these polymers are given in U.S. Pat. No. 4,909,986, issued Mar. 20, 1990, to N. Kobayashi and A. Kawazoe, incorporated herein by reference, in its entirety. Another example of water-soluble polymers containing both cationic and anionic functionalities is a copolymer of dimethyldiallyl ammonium chloride and acrylic acid, commercially available under the trade name Merquat 280® from Calgon.

While the aforementioned water soluble polymers are useful in the present invention, when using these materials, care must be taken to insure no residual acrylic acid is present due to safety concerns associated with the presence of acrylic acid.

Water-soluble alkali metal carbonate and/or bicarbonate salts, such as sodium bicarbonate, potassium bicarbonate, potassium carbonate, sodium carbonate, and mixtures thereof can be added to the composition of the present invention in order to help to control certain acid-type odors. Preferred salts are sodium carbonate monohydrate, potassium carbonate, sodium bicarbonate, potassium bicarbonate, and mixtures thereof. When these salts are added to the composition of the present invention, they are typically present at a level of from about 0.1% to about 5%, preferably from about 0.2% to about 3%, more preferably from about 0.3% to about 2%, by weight of the composition. When these salts are added to the composition of the present invention, it is preferred that incompatible metal salts not be present in the invention. Preferably, when these salts are used, the composition should be essentially free of zinc and other incompatible metal ions, e.g., Ca, Fe, etc. which form water-insoluble salts.

Aminocarboxylic acid chelating agents such as ethylenediaminetetraacetic acid (EDTA) can optionally be added to the composition of the present invention in order to enhance the activity of the water-soluble, antimicrobial preservative. When a chelating agent is added to the composition of the present invention, it is typically present at a level of from about 0.001% to about 0.3%, preferably from about 0.01% to about 0.2%, by weight of the composition.

Zeolites can also be used in the present invention. A preferred class of zeolites are characterized as "intermediate" silicate/aluminate zeolites, particularly for use in absorbing amine-type odors. "High" zeolites are preferred for control of sulfur-containing odors, e.g., thiols, mercaptans. Zeolites are explained more fully in U.S. Pat. No. 5,429,628, to Trinh et al., issued Jul. 4, 1995, which is incorporated herein by reference in its entirety.

The carbon material suitable for use in the present invention is the material well known in commercial practice as an absorbent for organic molecules and/or for air purification purposes. Often, such carbon material is referred to as "activated" carbon or "activated" charcoal. Such carbon is available from commercial sources under such trade names as; Calgon-Type CPG®; Type PCB®; Type SGL®; Type CAL®; and Type OL®.

Colorants and dyes can be optionally added to the odor absorbing compositions for visual appeal and performance impression. When colorants are used, care must be taken in the selection of choosing dye levels that will not color skin. Preferred colorants for use in the present compositions are highly water-soluble dyes, e.g., acid blue 3, acid blue 104, acid green 1, acid green 25, acid yellow 3, acid yellow 73 sodium salt, D&C green no. 5, 6 & 8, D&C yellow no. 7, 8, 10 & 11, D&C violet no. 2, FD&C blue No. 1 & 2, FD&C green no.3, FD&C yellow no. 5 & 6, and mixtures thereof Optionally, the present skin composition may also comprise known antiperspirants and/or other known deodorant compositions not explicitly disclosed previously. Examples of antiperspirants appropriate for aqueous solutions include aluminum-zirconium tetrachlorohydrex glycine, aluminum-zirconium pentachlorohydrate, aluminum sesquichlorohydrate, or aluminum chlorhydrate and mixtures thereof.

PROCESS OF MAKING COMPOSITIONS

The compositions used in the present method are prepared by a process comprising the steps of making a mixture of aqueous carrier and all ingredients (except dimethicone) by mixing until all are dissolved and the mixture is homogenous. The term "homogenous", as used herein, means uniformly dispersed throughout the mixture or solution. If dimethicone is used, the process of preparing the composition further comprises mixing the mixture with the dimethicone using high shear (for example using a mill) until the composition is homogenous.

Since the compositions of the present method are to be applied directly to the skin and/or hair, various applicators are useful for delivering the compositions to the entire body for maximum malodor control. For example, the compositions are preferably deposited on a paper product such as a wipe which later is contacted with the skin to transfer the composition to the skin.

Any wipe structures and/or methods of making the wipe structures commonly known in the art may be used in the present invention. The wipe comprises a flexible dispensing means. The term "flexible dispensing means", as used herein, refers to paper, cloth, non-woven substrates, films, foams, foam sheets, sponges, roller, pad, sponge, tissue, cotton ball, and the like. Preferred wipe substrates comprise a porous material, such as the non-woven substrates, foams, or sponges, which are capable of holding the composition within the pores of the substrates. Examples of cellulosic non-wovens particularly useful and economic in the present invention are described in U.S. Pat. No. 4,191,609, Trokhan, issued Mar. 4, 1980. Further description of useful wipes and methods of making said wipes are found in World Patent 95/17175, to Mitra et. al, publication date of Jun. 29, 1995. Both references pare incorporated herein by reference in their entireties.

Techniques for combining the wipe substrates with the odor-absorbing compositions of the present invention are well known in the art. Examples of common methods of combining the composition to the wipe substrate may involve coating, immersing, dipping, or spraying, the wipe substrate with the composition of the present invention. When dimethicone is included in the present invention, care must be taken to insure that the solution is mixed with high shear (such as milling) in order to obtain a homogenous solution immediately prior to application to the wipes. The composition of the present invention is added to the wipe substrate at level sufficient to provide the desired odor control and/or other desired skin benefits of the present invention. A convenient method of combining the composition of the present invention with the chosen substrate is to place the substrate inside an open package which will ultimately house the finished product until use. The composition is poured onto the substrate and allowed to distribute throughout. Where the composition comprises dimethicone, it is preferred that the homogenous composition is poured onto each wipe individually rather than onto a stack of wipes. The package is then closed and the wipes ready for use. Packages suitable for use herein are any packages commonly known in the art and include resealable packages and those suitable for one time use.

The composition of the present invention can also be delivered as a liquid via a spray dispenser or a bottle. Preferred is a manually activated spray dispenser to avoid the use of aerosols which may be irritating to sensitive areas of the body. Spray dispensers useful in the present invention are described more fully in U.S. Pat. No. 5,534,165, to Pilosof et al., issued Jul. 9, 1996, which is incorporated herein by reference in its entirety.

The following non-limiting examples illustrate the formulations and methods of use of the present invention.

| PERFUME COMPOSITION A | | PERFUME COMPOSITION B | |
|---|---|---|---|
| Ingredients | Wt. % | Ingredients | Wt. % |
| Anisic aldehyde | 2.53 | Allyl caproate | 0.8 |
| Benzyl acetate | 5.05 | Amyl acetate | 0.4 |
| Benzyl propionate | 1.26 | Anisic aldehyde | 0.8 |
| Beta gamma hexanol | 0.50 | Benzyl acetate | 5.0 |
| Cinnamic alcohol | 1.27 | Benzyl propionate | 2.1 |
| cis Jasmone | 0.50 | beta gamma Hexanol | 0.4 |
| Dihydro myrcenol | 6.32 | Cinnamic alcohol | 1.4 |
| Dimethyl benzyl carbinyl acetate | 3.78 | Citral | 5.1 |
| Eucalyptol | 1.77 | Citronelly nitrile | 2.1 |
| Geraniol | 12.63 | Dihydro myrcenol | 5.0 |
| Geranyl nitrile | 3.03 | Dimethyl benzyl carbinyl acetate | 2.1 |
| Hydroxycitronellal | 7.57 | Eucalyptol | 1.3 |
| alpha Ionone | 3.04 | Fenchyl alcohol | 1.7 |
| Iso bornyl acetate | 3.78 | Flor acetate | 6.1 |
| Ligustral | 0.51 | Frutene | 3.1 |
| Linalool | 6.31 | Geraniol | 4.2 |
| Linalyl acetate | 2.53 | Geranyl nitrile | 3.0 |
| Methyl benzoate | 0.50 | Hexanol | 0.4 |

-continued

| PERFUME COMPOSITION A | | PERFUME COMPOSITION B | |
|---|---|---|---|
| Ingredients | Wt. % | Ingredients | Wt. % |
| Methyl dihydro jasmonate | 7.58 | Iso bornyl acetate | 1.3 |
| Phenyl ethyl acetate | 1.26 | laevo Carvone | 0.4 |
| Phenyl ethyl alcohol | 14.90 | Linalool | 12.5 |
| Phenyl hexanol | 3.78 | Methyl anthranilate | 2.9 |
| Rose oxide | 0.76 | Methyl beta-naphthyl ketone | 4.2 |
| Terpineol | 7.58 | Methyl dihydro jasmonate | 20.7 |
| Vanillin | 1.26 | Methyl heptine carbonate | 0.1 |
| | | Nonyl aldehyde | 0.8 |
| | | Octyl alcohol | 2.1 |
| | | para Methoxy acetophenone | 1.3 |
| | | Phenyl ethyl alcohol | 8.3 |
| | | Camphor gum | 0.4 |

EXAMPLES I, I, and III

| Ingredients | Example I Wt. % | Example II Wt. % | Example III Wt. % |
|---|---|---|---|
| Tetrasodium EDTA | 0.10 | 0.10 | |
| Propylene glycol | 0.3 | 0.06 | |
| Zinc chloride | 1.00 | | |
| Zinc phenolsulfonate | | | 1.00 |
| Citric acid | 0.12 | 0.12 | 0.12 |
| Glydant ® Plus | 0.20 | 0.30 | |
| Suttocide ® A | 0.25 | | 0.50 |
| Hydroxypropyl beta-cyclodextrin | 5.00 | 1.00 | 3.00 |
| Dimethicone (100 centistoke) | 3.00 | 1.00 | |
| Perfume Composition* | 0.50 | 0.007 | 0.20 |
| Distilled Water | Balance | Balance | Balance |

*Either perfume composition A or B above can be used as the perfume composition for Examples I–III.

Prepare Examples I and II as follows: Add tetra sodium EDTA to approximately 66% of the distilled water for that formula and mix until dissolved. Then add each of the remaining ingredients, except for the dimethicone, in the order listed above, with mixing. Ensure that each ingredient is either dissolved or the solution is homogenous before adding the next ingredient. Add the remaining water of each of the total formulas and stir until homogenous. Finally, add the dimethicone using high shear until the mixture is homogenous.

Prepare Example III as follows: Add each of the ingredients in the order listed above, with mixing. Ensure that each ingredient is either dissolved or the solution is homogenous before adding the next ingredient. Finally, add the remaining water of each of the total formula and stir until homogenous.

Preparation for Application to Skin:

The solutions of the present invention, such as those formed from the examples may be loaded onto a wipe or poured into a spray device or poured directly onto the skin or cloth of the user's choosing for convenient application to the skin and/or hair.

To prepare wipes: Place dry fabric or wipe substance inside an open package which will ultimately contain the finished product. Where the composition comprises dimethicone, the mixture should once again be mixed vigorously to obtain a uniformly dispersed mixture. Pour the composition onto the fabric to distribute throughout. Close the package and seal for storage until consumer use as a wet wipe product.

To prepare spray: Pour the composition into the selected spray package. Close the package for storage until consumer use.

Example IV

A man is cooking fish and a spicy sauce requiring the dicing of garlic, onions, and various peppers. He is told that his hands and hair smell of these food odors and he wants to remove these odors from his body. The man rubs his hands and hair with wipes containing the composition in Example I. Each wipe deposits about 0.05 grams of environmental ordor-absorbing composition on the skin. The man notices less odor after using the wipes.

Example V

A woman finds that after she smokes a cigarette during a break at work, her hands and face smell of smoke and tobacco. She applies the composition from Example II via a pre-formed wipe. She tears open a sealed package and rubs the wipe (which is wet with the composition) on her face and hands. Each wipe deposits about 0.1 grams of environmental ordor-absorbing composition on the skin. The composition removes the residual smoke and tobacco odors which she found so disagreeable. This woman notices less odor and feels more comfortable returning to her desk after using the wipes.

Example VI

A man, on his way to an important meeting, stops to buy gasoline for his car. As he is filing the gas tank, gasoline splashes on his hands. The man wipes his hands on a paper towel but the gasoline odor remains on his hands. The man removes a small bottle from his gym bag which contains the composition of Example III. He opens the bottle and pours some of the composition on his hands, delivering roughly about 2.0 grams of the environmental odor-absorbing composition. He then smells his hands and notices that the gasoline odor is no longer present.

What is claimed:

1. A method of controlling environmental malodors on skin comprising the application to skin of a composition comprising:
   a. from about 0.1% to about 5%, by weight of the composition, of solubilized, water-soluble, uncomplexed cyclodextrin;
   b. from about 0.004% to about 2%, by weight of the composition, of a hydrophilic, volatile perfume composition comprising at least about 50% by weight of one or more hydrophilic, volatile perfume ingredients wherein each ingredient has a boiling point of about 260° or lower, and a ClogP of less than about 3.5; and
   c. an aqueous carrier.

2. The method of claim 1 wherein the composition is deposited on a wipe which comprises a flexible dispensing means.

3. The method of claim 2 wherein the composition further comprises from about 0.5% to about 30%, by weight of the composition, of a linear dimethicone having a nominal viscosity of 350 centistokes or less.

4. The method of claim 3 wherein the perfume composition comprises at least 5 different hydrophilic, volatile perfume ingredients.

5. The method of claim 4 wherein the uncomplexed cyclodexrin is selected form the group cosisting of hydroxy propyl beta cyclodextrin, methylated-beta-cyclodextrin, and mixtures thereof.

6. The method of claim 5 wherein the composition further comprises one or more optional components selected from the group consisting of low molecular weight polyols; water-soluble antimicrobial preservatives; zinc salts; water-soluble polymers; soluble carbonate and/or bicarbonate salts; chelating agents; zeolites; activated carbon; and mixtures thereof.

7. A method of controlling environmental malodors on skin comprising the application to skin of a composition comprising:
   a. from about 0.1% to about 5%, by weight of the composition, of solubilized, water-soluble, uncomplexed cyclodextrin;
   b. from about 0.01% to about 1%, by weight of the composition, of low molecular weight polyols;
   c. from about 0.004% to about 2%, by weight of the composition, of a hydrophilic, volatile perfume composition comprising at least about 55% by weight of one or more hydrophilic, volatile perfume ingredients wherein each ingredient has a boiling point of about 260° or lower, and a Clogp of less than about 3.5; and
   d. an aqueous carrier.

8. The method of claim 7 wherein the composition is deposited on a wipe which comprises a flexible dispensing means.

9. The method of claim 8 wherein the composition further comprises from about 0.5% to about 30%, by weight of the composition, of a linear dimethicone having a nominal viscosity of 350 centistokes or less.

10. The method of claim 9 wherein the perfume composition comprises at least 7 different hydrophilic, volatile perfume ingredients.

11. The method of claim 10 wherein the composition further comprises one or more optional components selected from the group consisting of water-soluble antimicrobial preservatives; zinc salts; water-soluble polymers; soluble carbonate and/or bicarbonate salts; chelating agents; zeolites; activated carbon; and mixtures thereof.

12. The method of claim 11 wherein the uncomplexed cyclodexrin is selected form the group cosisting of hydroxy propyl beta cyclodextrin, methylated-beta-cyclodextrin, and mixtures thereof.

13. A method of controlling environmental malodors on skin comprising the application to skin of a composition comprising:
   a. from about 0.1% to about 5%, by weight of the composition, of solubilized, water-soluble, uncomplexed cyclodextrin; and
   b. from about 0.01% to about 1%, by weight of the composition, of low molecular weight polyols;
   c. a safe and effective amount of solubilized, water-soluble, antimicrobial preservative;
   d. from about 0.004% to about 2%, by weight of the composition, of a hydrophilic, volatile perfume composition comprising at least about 55% by weight of at least 7 hydrophilic, volatile perfume ingredients wherein each ingredient has a boiling point of about 260° or lower, and a ClogP of less than about 3.5; and
   e. an aqueous carrier.

14. The method of claim 13 wherein the composition further comprises one or more optional components selected from the group consisting of zinc salts; water-soluble polymers; soluble carbonate and/or bicarbonate salts; chelating agents; zeolites; activated carbon; and mixtures thereof.

15. The method of claim 14 wherein the composition is delivered as a liquid by a spray bottle.

16. The method of claim 13 wherein the composition further comprises from about 0.5% to about 30%, by weight of the composition, of a linear dimethicone having a nominal viscosity of 350 centistokes or less.

17. The method of claim 16 wherein the composition is deposited on a wipe which comprises a flexible dispensing means.

* * * * *